United States Patent [19]

Fukuhara et al.

[11] Patent Number: 4,780,253

[45] Date of Patent: Oct. 25, 1988

[54] AROMATIZING DEVICE FOR AIR COMPRESSOR APPARATUS

[76] Inventors: Hiroshi Fukuhara; Katsumi Sueyoshi, both of c/o Fukuhara Seisakusho Co., Ltd. 4483-5 Akuwa-cho, Seya-ku, Yokohama, Kanagawa, Japan

[21] Appl. No.: 21,369

[22] Filed: Mar. 3, 1987

[30] Foreign Application Priority Data

May 19, 1986 [JP] Japan ............................ 61-75035[U]
Jun. 11, 1986 [JP] Japan ............................ 61-88884[U]
Jul. 4, 1986 [JP] Japan ............................ 61-103073[U]

[51] Int. Cl.⁴ .............................................. B01F 3/04
[52] U.S. Cl. .................................... 261/30; 261/78.2; 261/DIG. 65; 415/117; 422/124; 422/306
[58] Field of Search ............... 415/117; 422/123, 124, 422/306; 261/DIG. 65, 78.2, 30

[56] References Cited

U.S. PATENT DOCUMENTS

| | | | |
|---|---|---|---|
| 1,124,979 | 1/1915 | Waldeck | 422/123 |
| 2,118,327 | 5/1938 | Roberts | 422/124 |
| 2,523,373 | 9/1950 | Jennings et al. | 422/124 |
| 2,562,960 | 8/1951 | Stern | 422/123 |
| 2,614,820 | 10/1952 | Boydjieff | 422/306 |
| 2,966,312 | 12/1960 | Wilson, Jr. et al. | 184/55.2 |
| 3,009,542 | 11/1961 | Shada | 184/55.2 |
| 4,303,617 | 12/1981 | Bryson | 422/123 |
| 4,617,157 | 10/1986 | Stein et al. | 422/124 |

FOREIGN PATENT DOCUMENTS

| | | | |
|---|---|---|---|
| 939604 | 1/1984 | Canada | 422/306 |
| 2394298 | 2/1979 | France | 422/124 |

Primary Examiner—Tim Miles
Attorney, Agent, or Firm—Cushman, Darby & Cushman

[57] ABSTRACT

A aromatizing device for an air compressor which is mounted either in the compressor inlet or the feed tube between the compressor tank and pneumatic machinery. The air flows through a solid or liquid aromatizing agent in a chamber so that the agent is entrained therein to mask odors. The flow passage may be in parallel to the main passage and controlled to pass air and entrain agent for a predetermined time only following operation of the compressor.

5 Claims, 7 Drawing Sheets

AROMATIZING DEVICE FOR AIR COMPRESSOR APPARATUS

BACKGROUND OF THE INVENTION

1. Field of the Invention

The present invention relates to an aromatizing device for an air compressor apparatus and, more particularly, it relates to an aromatizing device arranged to feed an aromatic component into an air discharged from a pneumatic machinery which utilizes or controls a compressed-air supplied by the air compressor, such as air cylinder, air grinder, air driver, air valve or the like, or to feed an aromatic component into an atmosphere surrounding such pneumatic machinery.

2. Description of the Prior Art

As well known in the art, the pneumatic machinery as mentioned above is arranged to make use of the compressed-air supplied by the air compressor, to perform its own work. During working, the pneumatic machinery discharges the compressed-air into the atmosphere and the compressed-air thus discharged into the atmosphere produces an uncomfortable environment.

It is considered that such bad odor is produced on several reasons. One of the reasons resides in the fact that the compressed-air supplied by the air compressor itself contains bad odor. For example, in the case of the oil-lubricated air compressor the lubricant oil tends to be oxidized owing to heat of compression or heat of sliding friction to produce an oxidized oil or solid material such as carbon or tar. In the case of the oil-less air compressor, carbon particles tend to be produced by sliding movement. Accordingly, the compressed-air is contaminated thereby and thus there is produced an air containing bad odor, which is fed to the pneumatic machinery to operate the same and is discharged into the atmosphere as it is.

The other reason resides in the fact that the air compressor as well as the pneumatic machinery produces bad odor. For example, the air grinder tends to produce bad odor owing to generation of heat of friction.

Under such circumstances, in the fields where sanitary conditions are of importance, such as medical field, dental field, food article field, toilet article field or the like, the measure for avoiding the generation of such bad odor has been heretofore adopted. The measure which has been heretofore adopted resides in arranging a deodorizing device containing an odor absorbing agent on the way of a piping of an air compressor.

Although such deodorizing device containing odor absorbing agent has substantial deodorizing effect, the following problems are still left unsolved.

One of the problems is the fact that the odor absorbing agent used in the deodorizing device consists of activated charcoal, porous alumina, silica gel, synthetic zeolite, ion exchange resin having three-dimensional network atructure or the like and each of them has its own selective characteristic to a specific odor component, so that a specific odor absorbing agent is effective to deodorize some odorous component while it is not effective to deodorize other odorous component, with the result that some odorous component not absorbed by the odor absorbing agent may be discharged into the surrounding atmosphere. It in, therefore, required to selectively use an odor absorbing agent, depending upon the environment and kind of odor produced, but there are many kinds of odorous component, so that it is difficult, in fact, to eliminate 100% of bad odor.

The second problem resides in the fact that in the case of the deodorizing device using the odor absorbing agent, which is arranged on the way of the air passage of the air compressor, the bad odor is discharged into the surrounding atmosphere if the bad odor is produced from the pneumatic machinery which utilizes the compressed-air supplied by the air compressor.

SUMMARY OF THE INVENTION

The present invention was conceived on the discovery that adverse effects of bad odor can be avoided in more advantageous manner by producing some action of preventing or weakening the bad odor which may be sensed by people existing in surrounding atmosphere, as compared with removing the bad odor which is discharged into the environment surrounding the pneumatic machinery.

It is a main object of the present invention to provide a device which is arranged to feed an aromatic component into a compressed air discharged from an air compressor and to mask a bad odor contained in the compressed-air even if it is discharged from a pneumatic machinery residing at a terminal end of an air compressor apparatus.

In order to attain the main object as mentioned above, the present invention provides an aromatizing device for an air compressor which is characterized by including an air compressor driven by an electric motor, a tank connected to a discharge side of the air compressor and a compressed-air feeding tube connecting said tank with a pneumatic machinery, in which an aroma generating device containing an aromatizing agent is connected to a passage leading from an air inflow tube of said air compressor to said compressed-air feeding tube to feed an aromatic component into an air flowing through said passage.

The aromatizing agent as mentioned above includes all kinds of perfumery which may be liquid or solid. However, it is preferable that this aromatizing agent may be gasified and mixed into the surrounding air when it is fed into the air. The position where the aromatizing agent is fed into the compressed-air may be located on the way of the air inflow tube at the upstream side of the air compressor or it may be located on the way of the compressed-air feeding tube at the downstream side of the tank.

According to such arrangement, when the air compressor is driven by the electric motor and the compressed-air is supplied to the pneumatic machinery, an air flow is produced in the passage leading from the air inflow tube to the compressed-air feeding tube, so that the gasified aromatizing agent is fed by the aroma generating device into said air flow and mixed therewith. Accordingly. even if a bad odor is contained in the compressed-air discharged from the pneumatic machinery, it is masked by the aromatizing agent, so that people in the compressed-air discharging field may not sense the bad odor. Furthermore, it is possible to give a sweet smell to people in the surrounding environment by selecting a desired kind of the aromatizing agent.

It is another object of the present invention to provide a means for feeding an optimum amount of an aromatic component, depending upon an environment surrounding a pneumatic machinery. In other words, it is an object of the present invention to provide a means for feeding a variable controlled amount of an aromatic component to an air discharged from a pneumatic machinery. Thus, it is possible to provide a masking under an optimum condition to the environment surrounding the pneumatic machinery.

In order to attain the above object, the present invention provides an aromatizing device for an air compressor apparatus including an air compressor driven by an electric motor, a tank connected to a discharge side of said air compressor and a compressed-air feeding tube connecting said tank with a pneumatic machinery, said aromatizing device being arranged to feed an aromatic component to an air flowing through said compressed-air feeding tube and including a bypass tube arranged to bypass said compressed-air feeding tube, an aroma generating device containing an aromatizing agent and connected to a midway of said bypass tube to feed an aromatic component into an air flowing said bypass tube, and opening and closing valves arranged at an inlet and an outlet of said aroma generating device to open and close said inlet and outlet, whereby the aromatic component is fed into the compressed-air according to control of opening and closing operations of said valves. According to this arrangement, the compressed-air produced by the air compressor is temporarily stored in an air tank and then it is fed from the air tank through the compressed-air feeding tube to the pneumatic machinery, depending upon the use of the pneumatic machinery. If the valves at the inlet and the outlet of the bypass tube are in closed states, the compressed-air is not led into the bypass tube, so that no aromatic component is fed. When the above valves are opened, the compressed-air is introduced through the bypass tube into the aroma generating device, so that the aromatizing agent is gasified and mixed into the flow of the compressed-air. Thus the compressed-air containing the aromatic component is fed to the pneumatic machinery and even if the compressed-air discharged from the pneumatic machinery into the surrounding environment contains bad odor, it is masked by the aromatic component. Particularly, this device is so arranged that it does not always gasify the aromatizing agent from the aroma generating device and mix said component into the compressed-air but feeds the aromatizing agent only when the valves are opened. Consequently, it provides an optimum masking by controlling the opening time of the valves as desired.

It is another object of the present invention to provide a device in which the aromatic component is not passed through the pneumatic machinery, so that there is no possibility of the pneumatic machinery getting rust by the aromatic component, so that it can provide an optimum masking to the environment surrounding the pneumatic machinery at any time.

In order to attain the above object, the present invention provides an aromatizing device for an air compressor apparatus including an air compressor driven by an electric motor, a tank connected to a discharge side of said air compressor and a compressed-air feeding tube connecting said tank with a penumatic machinery, said atomizing device being arranged to feed an aromatic component to an air flowing said compressed-air feeding tube and including a branch tube connected to said compressed-air feeding tube, an aroma generating device containing an aromatizing agent to feed an aromatic component to an air flowing through said branch tube, and opening and closing valves arranged at one or both of an inlet and an outlet of said aroma generating device, whereby the aromatic component is fed to the environment surrounding the pneumatic machinery depending upon the control of opening and closing of said valves. According to this arrangement, the compressed-air produced by the air compressor is temporarily stored in an air tank and then it is fed from the air tank through the compressed-air feeding tube to the pneumatic machinery, depending upon the use of the pneumatic machinery. If one or both of the opening and closing valves arranged at the inlet and outlet of the aroma generating device in the branch tube are in closed state, the compressed air is not introduced into the brach tube, so that no aromatic component is fed. When one or both of the valves at the inlet and the outlet are opened, the compressed-air is introduced through the branch tube into the aroma generating device. Accordingly, the aromatizing agent is gasified and mixed into the compressed-air, so that the aromatizing agent is emitted into the environment surrounding the pneumatic machinery from the end of the branch tube. Particularly, this device is so arranged that it does not always gasify the aromatizing agent from the aroma generating device and mix said component into the compressed-air but feeds the aromatizing agent only when the valves are opened. Consequently, it provides an optimum masking by controlling the opening time of the valves as desired.

BRIEF DESCRIPTION OF THE DRAWINGS

The accompanying drawings illustrate several embodiments of the present invention, in which.

FIRST EMBODIMENT

Figure 1:
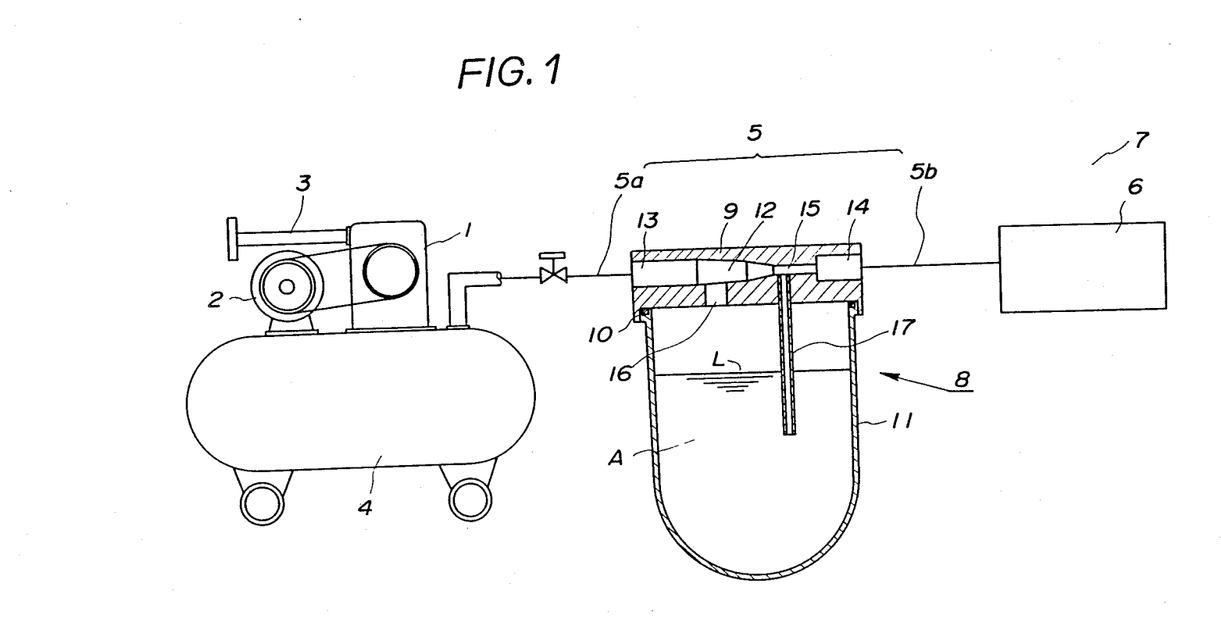
FIG. 1 is a systematic view, including a sectional view of an essential part, of the device according to a first embodiment of the present invention.

A first embodiment of this invention will now be described with reference to FIG. 1.

Numeral 1 shows an air compressor driven by a motor 2. Numeral 3 shows an air inflow tube. Numeral 4 shows a tank. When driving the motor 2, the air flowing in the air inflow tube 3 is compressed by the air compressor 1 and stored in the tank 4. Subsequently, it is supplied from the tank 4 to a pneumatic machinery such as air cylinder, air grinder, air driver, air pressure valve, air motor, etc. by way of a compressed-air supply tube 5. The thus used compressed-air is dischanged to an ambient environment 7.

The aforesaid means is a conventional one. According to this embodiment, an aroma generating device 8 is disposed in a preferred position of the compressed-air supply tube 5.

The aroma generating device 8 comprises a body 9 and an aromatizing agent storing chamber 11 disposed air-tightly below the body 9 by way of an O-ring 10. Formed in the body 9 is a compressed-air flow passage 12. The flow passage 12 is, at one end thereof, air-tightly connected to a primary side 5a of the compressed air supply tube 5, while, at the other end thereof, air-tightly connected to a secondary side 14 of the compressed-air supply tube 5. Further, the flow passage 12 is, at its nearly control part, provided with a throttled portion 15. Formed at an upstream side of the throttled portion 15 is an opening 16 for introducing into the aromatizing agent storing chamber 11 the compressed-air passing through the compressed-air supply tube 5. Further, disposed in the throttled portion 15 is an aromatizing agent outflow tube 17 which in open into the aromatizing agent storing chamber 17 where a liquid aromatizing agent A is stored at a liquid level L.

There are various kinds of liquid aromatizing agents A. As described previously, they are called "perfumes" "aromatics" or "masking agents". As examples of the perfumes or aromatic agents, there are natural perfumes (animal perfumes such as ja perfume, biyo perfume, kairi perfume, ambergris perfume; vegetable perfumes which are vapor-distilled from vegetable nuclei, branches, flowers, flower-buds, seedcases or seeds; synthetic perfumes which have been produced by a synthetic reaction such as oxidation or condensation of extracted perfumes and tar or pure synthetic raw materials for petrochemical products).

As an example, the vegetable natural perfumes include citronella oil, camfer oil, lemon glass oil, orange oil, pepermint oil, eucalyptus oil, lavender oil ocotilla oil, poidrose oil. bergamot oil, spearmint oil, lime oil, putiglen oil, clove oil, petiba oil, iran oil or the like.

As the synthetic perfumes, there are included, for example, benzene synthetic perfumes, artificial tenpene synthetic perfumes or the like.

As the masking agents, there are included additives in which a suitable timber acid liquid is added to the aforesaid perfumes.

In any event, it is important to select the best quality of aroma in accordance with the actual operational environment of the pneumatic machinery 6 and to remove any harmful material for human bodies.

An operation of this embodiment will now be described.

When driving the air compressor 1 by the motor 2, the air in supplied from the end of the air inflow tube 3, then the compressed-air is supplied to the tank 4 and stored therein. Farther, by driving the pneumatic machinery 8, the compressed-air within the tank 4 is introduced into the pneumatic machinery 6 by way of the compressed-air supply tube 5 at the primary side 5a, the flow passage 12 of the aroma generating device 8 and the compressed-air supply tube 5 at the secondary side 5b.

In the aforesaid process, since the compressed-air passes through the throttled portion 15, its sectional area of flow passage is reduced, the upper pressure of the aromatizing agent outflow tube 17 is descended. On the other hand, since the compressed air within the compressed-air supply tube 5 at the primary side is supplied at the liquid level L of the aromatizing agent A stored in the chamber 11, there arises a differential pressure between the pressure at the liquid level L and the upper pressure of the aromatizing agent outflow tube 17, thereby the aromatizing agent is sucked and discharged in a vaporized condition to the throttled portion 15 by way of the outflow tube 17.

As a result, the aromatizing agent is admixed with the compressed-air flowing in the flow passage 12, whereby the compressed-air containing an aromatic component is supplied into the pneumatic machinery which is under operation. After that, it is discharged to the environment.

Under such circumstances, even if any uncomfortable oder will occur from the air compressor itself and/or the pneumatic machinery itself, it can be masked by the aromatic component, so that those who stay at the place thereof do not feel at all uncomfortably, but may enjoy a good feeling from time to time. Further, when the aromatizing agent a within the aromatizing agent storing chamber 11 is consumed, it is possible to fill a certain amount of aromatizing agents into the chamber 11 from an inlet. The ratio of the compressed-air and the aromatizing agent contained therein is not described, but by disposing an orifice in the aromatizing agent outflow tube 17 to control flow rate, it is possible to regulate its ratio from the outside.

SECOND EMBODIMENT

Figure 2:
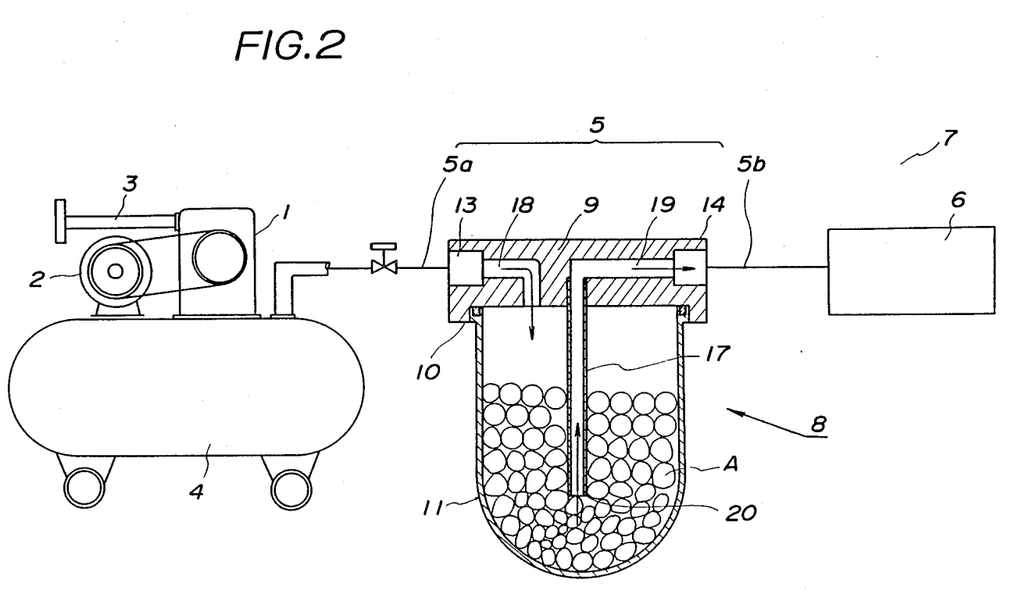
FIG. 2 is a systematic view, including a sectional view of an essential part, of the device according to a second embodiment of the present invention.

A second embodiment of this invention will now be described with reference to FIG. 2.

In this embodiment, the aromatizing agent A comprises a plurality of solid masses. The liquid perfumes and aromatic substances discribed in the second embodiment are transformed into the solid masses by adding a binder therein. In this case, either the binder or a basis material should be evaporated gradually under the pressure of the compressed-air.

The flow passage formed in the body 9 of the aroma generating device 8 has the following construction unlike the first embodiment.

There is disposed a primary side flow passage 18 to introduce the compressed-air supplied by the compressed-air supply tube 5 at the primary side 5a into the chamber 11 in which are stored solid massive aromatizing agents A. On the other hand, there is disposed a secondary side flow passage 19 to discharge the compressed air supplied into the aromatizing agent storing chamber 11 into the secondary side compressed-air supply tube 5b.

The secondary side flow passage 19 is communicated with the aromatizing agent outflow tube 17, and an end of the aromatizing agent outflow tube 17 is inserted into the solid massive aromatizing agents A. In case the components in the first and second embodiments are substantially the same contents, they are denoted with the same numerals.

Under such circumstances, the compressed-air supplied from the primary side compressed-air supply tube 5a is introduced into the solid massive aromatizing agent A by way of the primary flow passage 18, and then the solid massive aromatizing agents A are evaporated. Therefore, the aromatic component is added to the compressed-air in the chamber 11. The compressed-air mixed with the aromatic component is discharged from the secondary side compressed-air supply tube 5b by way of the aromatizing agent outflow tube 17 and the secondary side flow passage 19, and introduced into air pressure device 6.

Accordingly, even if any uncomfortable oder will occur form the air compressor and/or the pneumatic machinery, those who stay at the place thereof do not feel any bad oder in the compressed-air discharged to the environment from the pneumatic machinery.

In the embodiment, the aromatizing agents are the solid massive one, but they may be granular to the extent that they cannot be scattered easily.

THIRD EMBODIMENT

Figure 3:
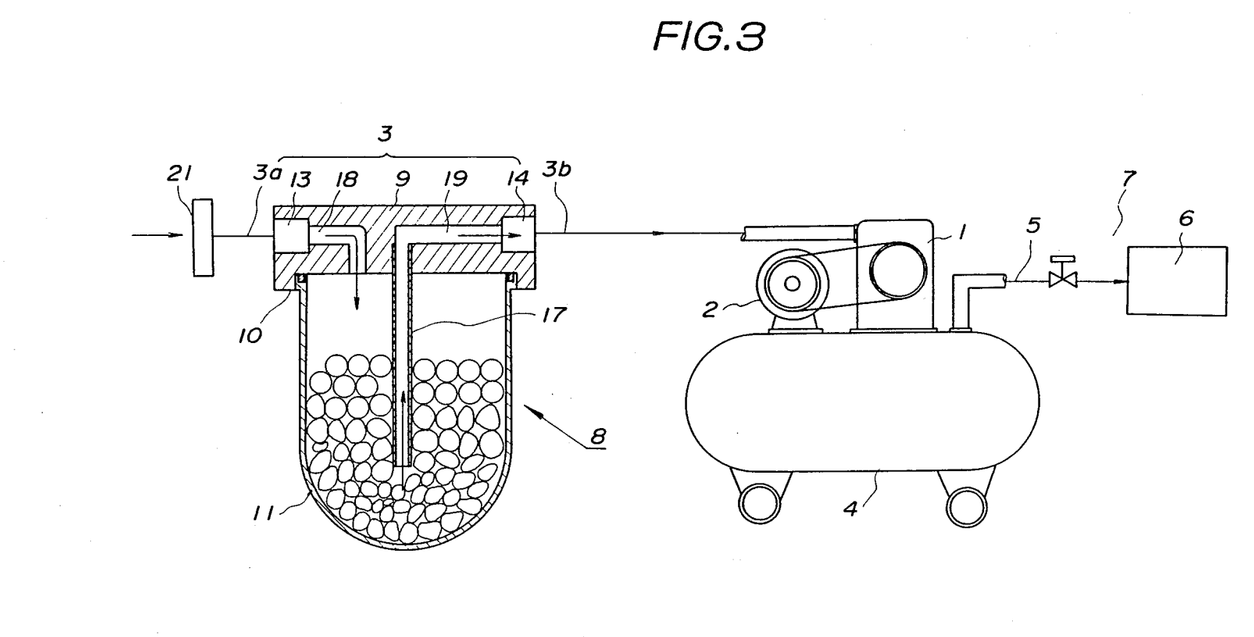
FIG. 3 is a similar systematic view showing the device according to third embodiment of the present invention.

A third embodiment of this invention will now be described with reference to FIG. 3.

This embodiment is a modified one of the second embodiment, in which the aroma generating device 8 is disfosed in a preferred position of the air inflow tube 3 of the upstream side of the air compressor 3. The aromatizing agents A are the solid massive ones.

Accordingly, the primary side flow passage 18 of the body 9 of the aroma generating device 8 is connected to a primary side air inflow tube 3a, while the secondary side flow passage 19 is a secondary side air inflow tube 3b. In case the components in the first and second embodiments are substantially the same contents they are denoted with the same numerals.

According to this embodiment, when the air compressor 1 is driven, the compressed-air is supplied into the primary side flow passage 3a through an air filter, and introduced into the solid massive aromatizing agents A of the chamber 11. The compressed-air is evaporated gradually and mixed with the aromatic component, and supplied into the secondary side air inflow tube 3b by way of the secondary side flow passage 19.

Thus, the compressed-air mixed with the aromatic component is introduced into the pneumatic machinery 6 by way of the tank and the compressed-air supply tube 5. Thus, any bad oder in the compressed-air to be discharged can be masked in the same way as described in the aforesaid embodiments.

FOURTH EMBODIMENT

Figure 4:
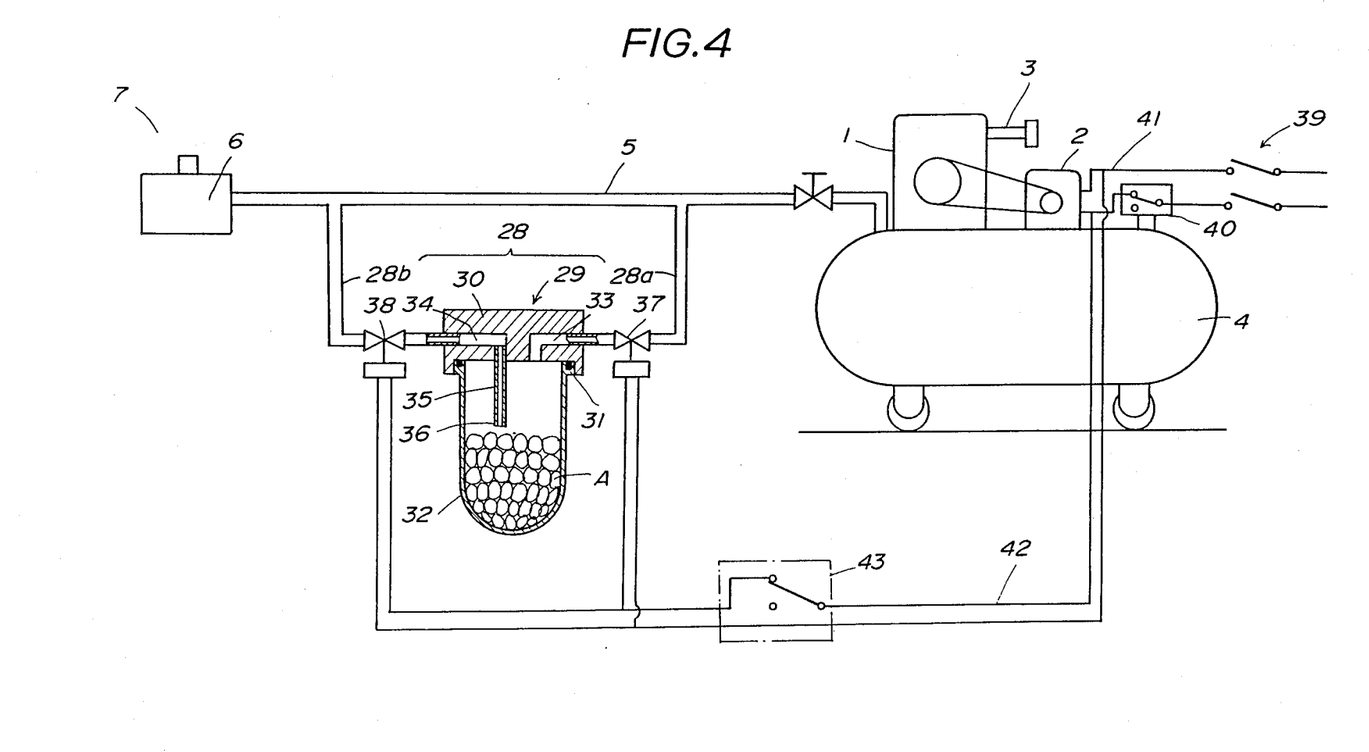
FIG. 4 is a similar systematic view showing the device according to a fourth embodiment of the present invention.

A fourth embodiment of this invention will now be described with reference to FIG. 4.

A by-pass tube 28 is disposed in a preferred position of the compressed-air supply tube 5. Disposed in the by-pass tube 28 is an aroma generating device 29.

The aroma generating device 29 comprises a body 30 and an aromatizing agent storing chamber 32 disposed air-tightly below the body 30 by way of an O-ring 31. The body 30 is provided with a primary side flow passage 33 to introduce into the aromatizing agent storing chamber 32 the compressed-air supplied from a primary side by-pass tube 28a. On the other hand, the body is provided with a secondary side flow passage 34 to discharge to a secondary side by-pass tube 28b, i.c., to the pneumatic machinery 6 the compressed-air which is introduced into the chamber 32. The secondary side flow passage 34 is communicated with an aromatizing agent outflow tube 35. An end 36 of the aromatizing agent outflow tube 35 is directed onto the solid massive aromatizing agents.

In this embodiment, an inlet of the aroma generating device 29, i.c., the primary side by-pass tube 28a and an outlet thereof, i.e., the secondary side by-pass tube 28b are respectively provided with switching valves 37 and 38.

The switching valves 37, 38 are electromagnetic valves to be switched on at the time of energizing. The electromagnetic valves are controlled by the following electric system.

The motor 2 is energized by a power source switch 39 and a pressure switch 40. A secondary power supply line 42 branched from a downstream side of the pressure switch 40 of a main power supply line 41 is connected to the electromagnetic valves 37, 38 respectively by way of a variable timer 43. The variable timer 43 transmits output signals at the energizing time, is switched off after a lapse of the preset time (e.g. 10 seconds) and maintains such a condition. When the pressure switch 40 is switched off, the variable timer 43 is returned to an initial condition.

An operation of this embodiment will be discribed.

When the power source switch 39 is turned on, the motor 2 is driven in the case the pressure in the air tank 4 is below the predetermined value and the pressure switch 20 is in "ON". Accordingly, the air compressed by the air compressor 1 is temporarily stored in the air tank 4 and introduced into the pneumatic machinery 6 by way of the compressed-air supply tube 5. Then, power is supplied to the variable timer 43 by way of the secondary power supply line 42. Accordingly, the variable timer 43 is switched on, and the electromagnetic valves 37, 38 are energized and open. Therefore, a part of the compressed-air passing through the compressed-air supply tube 5 flows in the primary by-pass tube 28a and enters into the chamber 32 of the aroma generating device 29. Thus, the aromatizing agents A are evaporated, the evaporated aromatizing agents A are mixed with the compressed-air and such mixed air is supplied to the compressed-air supply tube 5 by way of the secondary by-pass tube 28b, where it is mixed again with the compressed-air passing through the compressed-air supply tube 5 and then supplied into the pneumatic 6.

After a lapse of the preset time (e.g. 10 seconds) of the variable timer 43, it is switched off and both the electromagnetic valves 37 and 38 are closed, so that access of the compressed-air to the aroma generating device 29 is suspended. Accordingly, no supply of the aromatic component to the pneumatic machinery 6 is made.

Thus, only during the predetermined time of the variable timer 43, the aromatic component is supplied to the air pressure dvevice 6 and discharged therefrom to the environment. Accordingly, by seting ON time of the variable timer at the optimum interval, the optimum quantity of the aromatic component can be supplied to the environment of the pneumatic machinery.

Further, when the pressure of the compressed-air in the tank 4 exceeds a predetermined value, the pressure switch 40 is OFF and the variable timer 43 is automatically returned to the initial condition. Thus, when the pressure switch 40 is turned on, the aforesaid operation is again repeated.

Although the solid massive aromatizing agents A are employed in this embodiment, the liquid aromatizing agent may, of course, be done.

FIFTH EMBODIMENT

Figure 5:
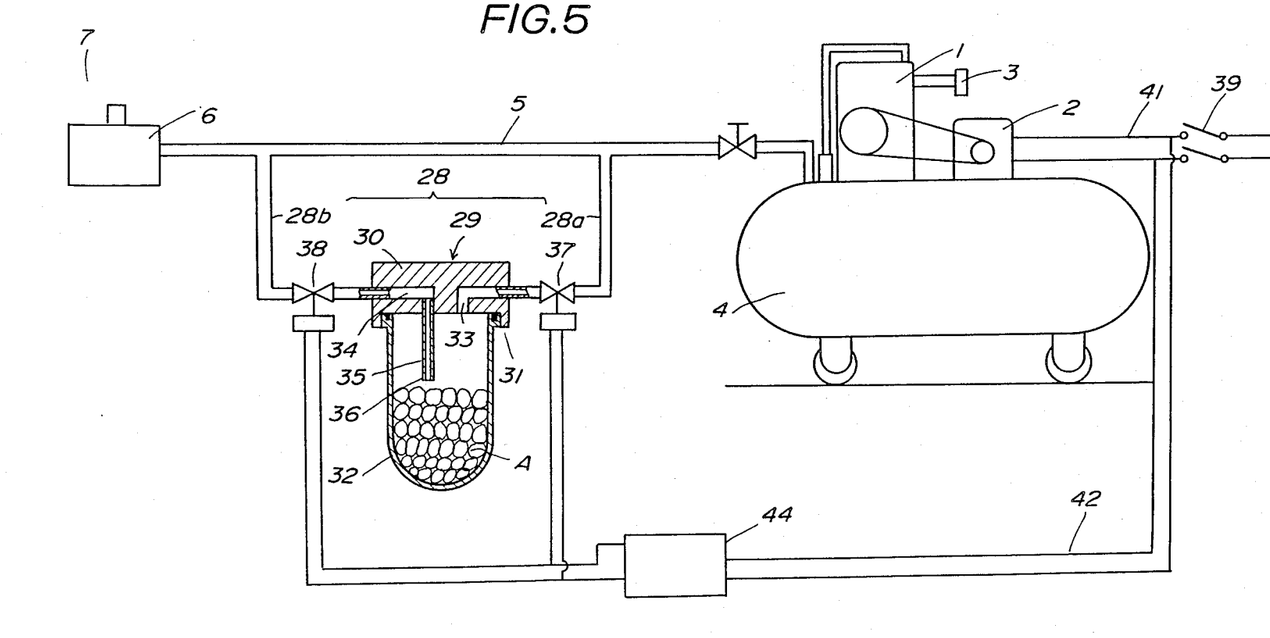
FIG. 5 is a similar systematic view showing the device according to a fifth embodiment of the present invention.

A fifth embodiment of this invention will now be described with reference to FIG. 5.

This embodiment is substantially semilar to the fourth embodiment. According to a remarkable aspect of this invention, the timer control of the electromagnetic valves 37, 38 which open at the energizing time in carried out by a cycle timer 44. The same components in the fourth and fifth embodiments are denoted by the same numerals.

The energizing time and non-energizing time of the cycle timer 44 may be controlled at will in accordance with the enviromental conditions. Under such circumstances, an inlet of and an outlet of the aroma generating device 29 can be opened or closed, so that the quantity of the aromatizing agents to be supplied to the pneumatic machinery 29 can be regulated minutely.

In this embodiment, power of the cycle timer 44 is supplied by the main power supply line 41, but it may be done by another power supply line.

Further, a plurality of by-pass tubes may be disposed in parallel with each other, in each of which may be disposed such aroma generating device 29 and the switching valves 37 and 38. Thus, it is possible to employ a plurality of aroma generating devices selectively.

SIXTH EMBODIMENT

Figure 6:
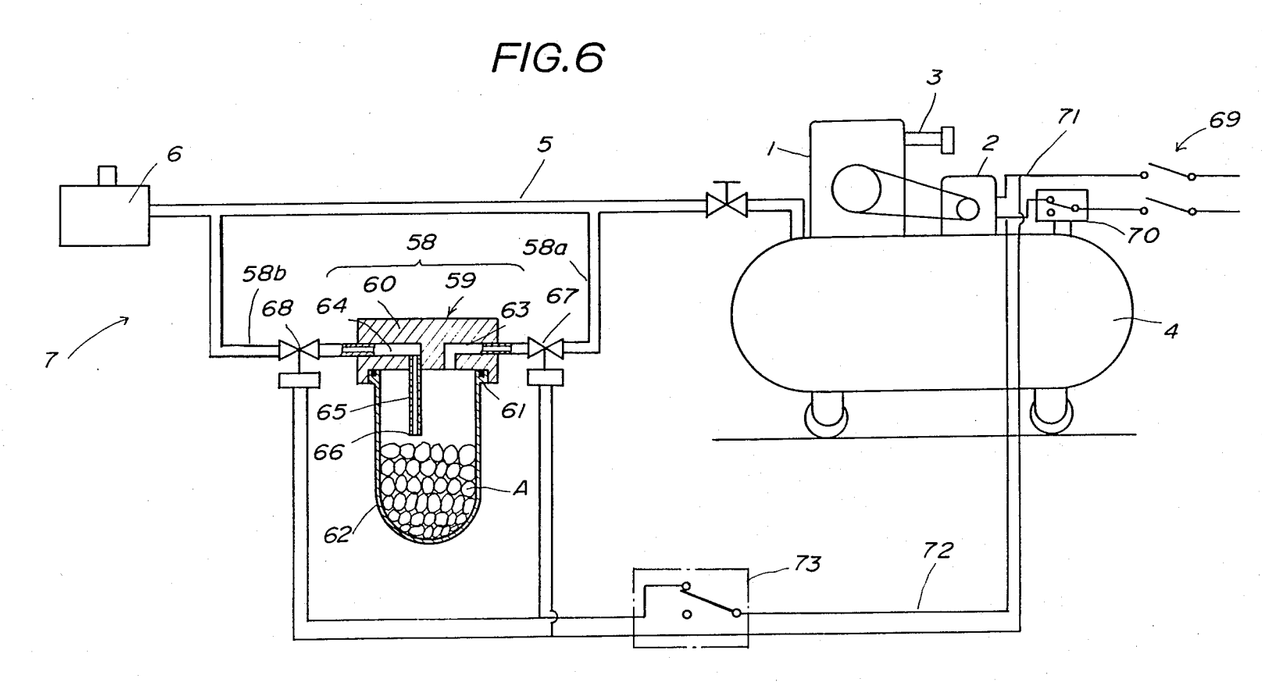
FIG. 6 is a similar systematic view showing the device according to a sixth embodiment of the present invention.

A sixth embodiment of this inwention will now be described with reference to FIG. 6.

A branch tube 58 is disposed in a preferred position of the compressed-air supply tube 5. The branch tube 58 comprises the following aroma generating device 59.

The device 59 comprises a body 60 and an aromatizing agent storing chamber 62 disposed air-tightly below the body 60 by way of O-ring 61. The body 60 is provided with a primary side flow passage 63 to introduce to an aromatizing agent storing chamber 62 the compressed-air supplied from a primary side branch tube 58a. On the other hand, the body 63 is provided with a secondary side flow passage 64 to discharge to a secondary side branch tube 58b the compressed air introduced into the chamber 62.

The secondary side flow passage 64 is communicated with an aromatizing agent outflow tube 65, and an end 66 of the outflow tube 65 is directed onto the solid massive aromatizing agents A.

In this embodiment, an inlet of the aroma generating device 59 i.c. the primary side branch tube 58a and an out thereof i.c. the secondary side branch tube 58b are respectively provided with switching valves 67 and 68.

In this embodiment, the switching valves 67, 68 are electromagnetic valves to be switched on at the energizing time. The electromagnetic valves are controlled by the following electric system.

The motor 2 is energized by a power source switch 69 and a pressure switch 70. A secondary power supply line 72 branched from a downstream side of the pressure switch 70 of a main power supply line 71 is connected to the electromagnetic valves 67 and 68 respectively by way of a variable timer 73. The variable timer 73 transmits output signals at the energizing time, is switched off after a lapse of the preset time (e.g. 10 seconds) and maintains such a condition. When the pressure switch 40 is switched off, the variable timer 43 is returned to an initial condition.

An operation of this embodiment will be described.

When the power source switch 69 is turned on, the motor 2 is driven in the case the pressure in the air tank 4 is below the predetermined value and the pressure switch 70 is in "ON". Accordingly, the air compressed by the air compressor 1 is temporarily sotred in the air tank 4 and introduced into the pneumatic machinery 6 by way of the compressed-air supply tube 5. Then, power is supplied to the variable timer 73 by way of the secondary power supply line 72. Accordingly, the variable timer 73 is switched on, and the electromagnetic valves 67, 68 are energized and open. Therefore, a part of the compressed-air passing through the compressed-air supply tube 5 flows in the primary by-pass tube 58a and enters into chamber of the aroma generating device.

Thus, the aromatizing agents A are evaporated, the evaporated aromatizing agents A are mixed with the compressed-air and such mixed air is supplied to the compressed-air supply tube 5 by way of the secondary by-pass tube 58b where it is mixed again with the compressed-air passing through the compressed-air supply tube 5 and then supplied into the pneumatic machinery 6.

After a lapse of the preset time (e.g. 10 seconds) of the variable timer 73, it is switched off and both the electronic magnetic valves 67 and 68 are closed, so that access of the compressed-air to the aroma generating device 59 is suspended. Accordingly, no supply of the aromatic content to the air pressure device 6 is made.

Thus, only during the predetermined time of the variable timer 73 the aromatic component is supplied to the pneumatic machinery 6 and discharged therefrom to the environment. Accordingly, by setting ON time of the variable timer at the optimum interval, the optimum quantity of the aromatic component can be supplied to the environment of the pneumatic machinery.

Further, when the pressure of the compressed-air in the tank 4 exceeds a predetermined value, the pressure switch 70 is OFF and the variable time 73 in automatically returned to the initial condition. Thus, when the pressure switch 70 is turned on, the aforesaid operation is repeated.

Although the solid massive aromatizing agents A are employed in this embodiment, the liquid aromatizing agent may, of course, be used.

SEVENTH EMBODIMENT

Figure 7:
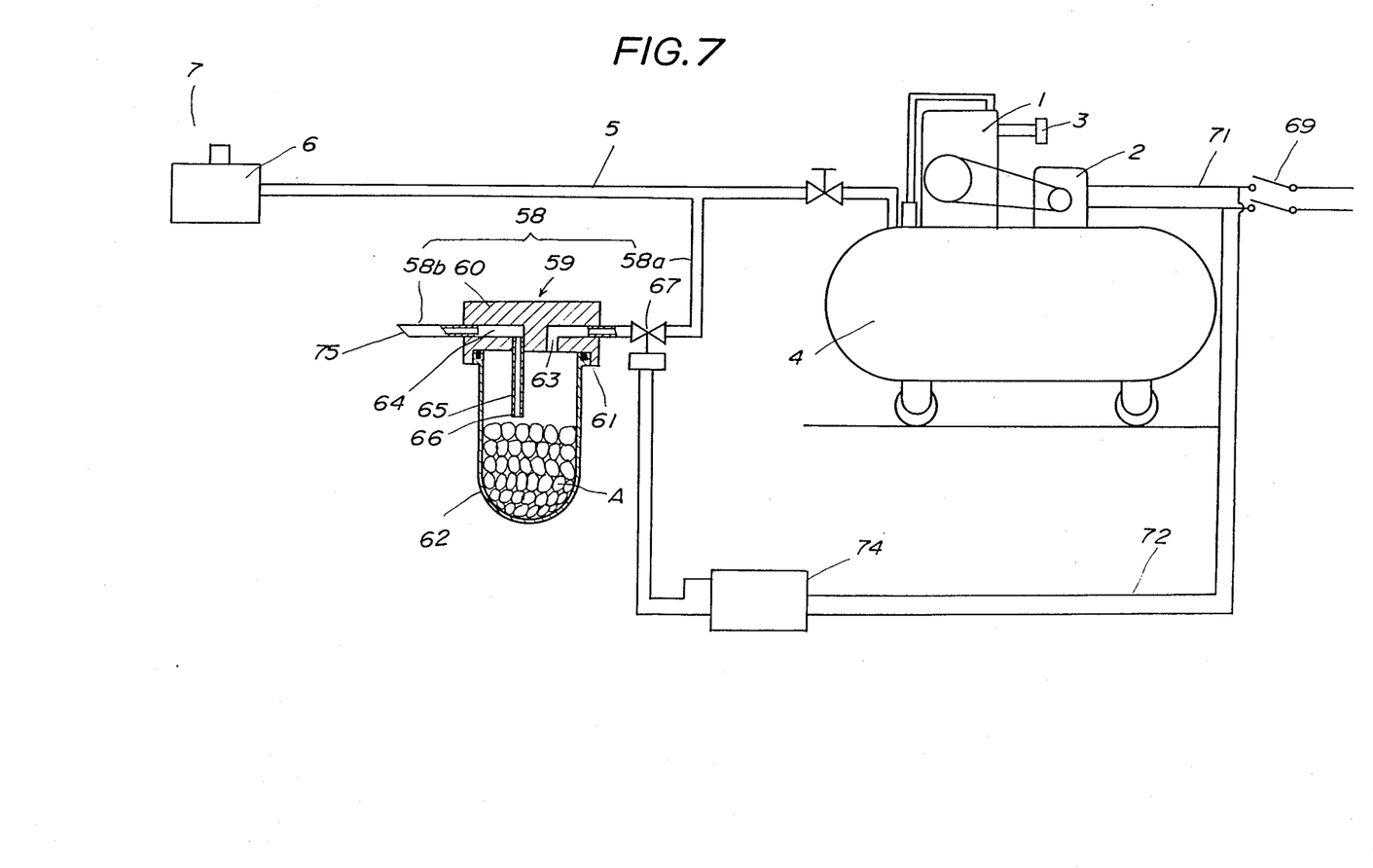
FIG. 7 is a similar systematic view showing the device according to a seventh embodiment of the present invention.

A seventh embodiment of this invention will now be described with reference to FIG. 7.

This embodiment is substantially similar to the sixth embodiment.

Namely, one electromagnetic valve 67 which open at the energizing time is disposed at the inlet side of the aroma generating device 59. The timer control of the electromagnetic valve 87 is carried out by a cycle timer 74. The same components in the sixth and seventh embodiments are denoted with the same numerals.

The energizing time and non-energizing time of the cycle timer 74 may be controlled at will in accordance with the environmental conditions. Under such circumstances the inlet of the aroma generating device 59 can be opened or closed, so that the quantity of the aromatizing agents to be supplied to the environment 7 of the pneumatic machinery 6 can be regulated minutely.

In this embodiment, power of the cycle timer 74 is supplied by the main power supply line 71, but it may be done by another power supply line.

Further, a plurality of branch tubes may be disposed in parallel with each other, in each of which may be disposed such aroma generating device 59 and the switching valves. Thus, it is possible to employ a plurality of aroma generating devices selectively.

We claim:

1. An aromatizing device for an air compressor system having an air compressor with an air inlet, an electric motor for driving said compressor, a tank coupled to a discharge side of the compressor and a compressed air tube for connecting said tank with pneumatic machinery, said device comprising:

means defining a chamber for holding a quantity of aromatizing agent and having an inlet and an outlet;

means for connecting said chamber in a bypass flow path in parallel with said air tube including electrically operable valve means for opening and closing said bypass path; and control means for opening said valves means for a predetermined time in response to operation of said compressor so that air is partially and temporarily diverted through said bypass path to entrain said agent therein and mask odors.

2. A device as in claim 1 further including a quantity of solid aromatizing agent.

3. A device as in claim 2 wherein said means for connecting includes a body defining a first passage between said air tube and a first opening into said chamber, and a second passage between said machinery and a second opening into said chamber and a tube extending from one of said openings into said agent.

4. A device as in claim 1 wherein said control means includes means for detecting the pressure in said tank, said control means operating said valve means when said pressure drops below a predetermined value.

5. A device as in claim 1 wherein said control means includes a cyclical timer for periodically opening and closing said valves.

* * * * *